(12) United States Patent
Rapaka et al.

(10) Patent No.: US 10,918,309 B2
(45) Date of Patent: Feb. 16, 2021

(54) ARTIFICIAL INTELLIGENCE-BASED COPD ASSESSMENT

(71) Applicant: Siemens Healthcare GmbH, Erlangen (DE)

(72) Inventors: Saikiran Rapaka, Pennington, NJ (US); Justin Hodges, Orlando, FL (US); Puneet Sharma, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 98 days.

(21) Appl. No.: 16/381,100

(22) Filed: Apr. 11, 2019

(65) Prior Publication Data

US 2020/0323464 A1 Oct. 15, 2020

(51) Int. Cl.
| | | |
|---|---|---|
| *G06K 9/00* | (2006.01) | |
| *A61B 5/091* | (2006.01) | |
| *G16H 50/50* | (2018.01) | |
| *G16H 50/30* | (2018.01) | |
| *G16H 50/20* | (2018.01) | |
| *G16H 10/20* | (2018.01) | |

(Continued)

(52) U.S. Cl.
CPC ............ *A61B 5/091* (2013.01); *A61B 5/087* (2013.01); *G06N 3/08* (2013.01); *G16H 10/20* (2018.01); *G16H 50/20* (2018.01); *G16H 50/30* (2018.01); *G16H 50/50* (2018.01); *A61B 5/0033* (2013.01); *G06N 20/00* (2019.01); *G16H 10/60* (2018.01)

(58) Field of Classification Search
None
See application file for complete search history.

(56) References Cited

U.S. PATENT DOCUMENTS

| 7,517,320 B2* | 4/2009 | Wibowo | A61B 5/02007 600/529 |
|---|---|---|---|
| 2005/0105788 A1* | 5/2005 | Turek | G06F 19/321 382/131 |

(Continued)

FOREIGN PATENT DOCUMENTS

| EP | 3404666 A2 | 11/2018 |
|---|---|---|
| WO | WO2009102930 A2 | 8/2009 |
| WO | WO2011056684 A2 | 5/2011 |

OTHER PUBLICATIONS

Extended European Search Report (EESR) dated Jul. 17, 2020 in corresponding European Patent Application No. 20168682.1.

(Continued)

*Primary Examiner* — Shervin K Nakhjavan (57) ABSTRACT

For COPD assessment in medical imaging, imaging data is used to model airways and to extract values for features representative of COPD. The airway model provides values for anatomy of the airways and/or airflow. The values of anatomy, airflow, and/or extracted image features in combination indicate COPD information A machine-learned model may be used to relate the anatomy, airflow, and/or extracted image features to the COPD information. Additional information may be used, such as spirometry results and/or questionnaire answers. The combination of information, including airway modeling, as input to a COPD model may provide a more comprehensive understanding of COPD for assistance in therapy and/or diagnosis of a particular patient.

20 Claims, 3 Drawing Sheets

(51) Int. Cl.
  *A61B 5/087*   (2006.01)
  *G06N 3/08*    (2006.01)
  *G16H 10/60*       (2018.01)
  *G06N 20/00*       (2019.01)
  *A61B 5/00*        (2006.01)

(56) References Cited

U.S. PATENT DOCUMENTS

| | | | | |
|---|---|---|---|---|
| 2010/0063410 | A1* | 3/2010 | Avila | A61B 5/7275 |
| | | | | 600/532 |
| 2011/0280457 | A1* | 11/2011 | Nielsen | G06T 7/44 |
| | | | | 382/131 |
| 2012/0072193 | A1* | 3/2012 | De Backer | A61M 16/021 |
| | | | | 703/2 |
| 2012/0082358 | A1* | 4/2012 | Kiraly | G06T 7/0014 |
| | | | | 382/131 |
| 2013/0004044 | A1* | 1/2013 | Ross | G06T 7/136 |
| | | | | 382/131 |
| 2013/0331290 | A1* | 12/2013 | Keller | C12Q 1/6883 |
| | | | | 506/9 |
| 2015/0351714 | A1* | 12/2015 | De Backer | A61N 5/10 |
| | | | | 600/427 |
| 2016/0184013 | A1* | 6/2016 | Brannan | A61B 18/14 |
| | | | | 600/424 |
| 2016/0328850 | A1* | 11/2016 | Yin | G16H 30/40 |
| 2017/0329927 | A1 | 11/2017 | Taherian et al. | |
| 2019/0057505 | A1* | 2/2019 | Pheiffer | G06T 7/136 |
| 2019/0290225 | A1* | 9/2019 | Dunican | C12Y 301/21001 |
| 2020/0069219 | A1* | 3/2020 | Hoppmann | A61B 5/0826 |
| 2020/0135334 | A1* | 4/2020 | Rajasekhar | H04M 3/4936 |

OTHER PUBLICATIONS

Sorensen L et al: "Texture-Based Analysis of COPD: A Data-Driven Approach"; IEEE Transactions on Medical Imaging, IEEE Service Center, Piscataway, NJ, US, vol. 31, No. 1, Jan. 1, 2012, pp. 70-78.

Ching-Long, Lin et al: "Computational fluid dynamics", IEEE Engineering in Medicine and Biology Magazine, IEEE Service Center, Piscataway, NJ, US, vol. 28, No. 3, May 1, 2009, pp. 25-33.

Barbosa Jr, Eduardo J. Mortani, et al. "Machine learning algorithms utilizing quantitative ct features may predict eventual onset of bronchiolitis obliterans syndrome after lung transplantation." Academic radiology 25.9 (2018).

Clukers, J., et al. "Quantitative CT analysis using functional imaging is superior in describing disease progression in idiopathic pulmonary fibrosis compared to forced vital capacity." Respiratory research 19.1 (2018).

Hajian, Bita, et al. "Changes in ventilation—perfusion during and after an COPD exacerbation: an assessment using fluid dynamic modeling." International journal of chronic obstructive pulmonary disease 13 (2018).

Lanclus, Maarten, et al. "Machine Learning Algorithms Utilizing Functional Respiratory Imaging May Predict COPD Exacerbations." Academic radiology (2018).

* cited by examiner

ARTIFICIAL INTELLIGENCE-BASED COPD ASSESSMENT

BACKGROUND

The present embodiments relate to chronic obstructive pulmonary disorder (COPD). COPD is an obstructive lung disease caused due to poor airflow. Two main underlying causes for COPD are emphysema and airway disease (e.g., bronchitis). Predictions for the year 2020 are that COPD will be #3 in morbidity and #5 in mortality (globally).

COPD may be diagnosed based on a preliminary questionnaire and then breathing measurements both with and without inhaled medication (spirometry), if warranted from the questionnaire results. The questionnaire information covers a wide range of information, including family history, history of symptoms and habits (e.g. smoking), history of diseases and respective severity (e.g. asthma, cancer, etc.), activity level, and general health metrics. The main outputs of the spirometry test are Forced Expiratory Value in 1 second (FEV1) and Forced Vital Capacity (FVC). These values are normalized based on demographic distribution.

The Global Initiative for Chronic Obstructive Lung Disease (GOLD) provides the criteria used to quantify COPD severity. These criteria are two spirometry metrics ($FEV_1$ and FVC) and usually 1-3 symptom related to pieces of information from questionnaire. In some cases, computed tomography (CT) is used to evaluate the disease severity, specifically in distal portions of the airway for emphysema.

A comprehensive understanding of COPD is still lacking. This lack of understanding has widespread ramifications, such as predicting disease progression and worsening symptoms (e.g. sudden outbreaks which require hospitalization, termed 'exacerbations'), treatment related actions (e.g. inhaled medications), and how patients can best go on living with a high quality of life (e.g. being capable of living an active life, indoor/outdoor air pollution), to name a few. Another example is in regard to COPD treatment. Often, patients take medications on an ongoing basis without improvement, whereby small and subtle changes in the airway itself may enable noticeable improvement in symptoms.

SUMMARY

By way of introduction, the preferred embodiments described below include methods, computer readable media, and systems for COPD assessment in medical imaging. Imaging data is used to model airways and to extract values for features representative of COPD. The airway model provides values for anatomy of the airways and/or airflow. The values of anatomy, airflow, and/or extracted image features in combination indicate COPD information A machine-learned model may be used to relate the anatomy, airflow, and/or extracted image features to the COPD information. Additional information may be used, such as spirometry results and/or questionnaire answers. The combination of information, including airway modeling, as input to a COPD model may provide a more comprehensive understanding of COPD for assistance in therapy and/or diagnosis of a particular patient.

In a first aspect, a method is provided for chronic obstructive pulmonary disorder (COPD) assessment in a medical imaging system. A medical scanner scans a lung of a patient, providing first imaging data representing a multi-dimensional region of the lungs of the patient. An image processor models airways of the lung of the patient from the first imaging data, providing a value for airflow in the airways. The image processor determines COPD information from a machine-learned model in response to input of the value for the airflow, a patient questionnaire answer, a spirometry result, and a value of a feature represented in the first imaging data. The COPD information for the patient is displayed.

In one embodiment, a computed tomography system scans a three-dimensional region of the patient.

The modeling may include segmenting the airways of the lung from the first imaging data and/or performing computational flow dynamics for the airways. The value for the airflow may be a stress, pressure, velocity, or volume value. In other embodiments, the modeling is of a first portion of the airways with a three-dimensional model and of a second portion of the airways with a reduced order model. The second portion has the airways with smaller diameters than the airways of the first portion.

The determined COPD information may be a COPD severity, COPD quantification, COPD diagnosis, COPD therapy, or combinations thereof. The COPD information may be determined in response to texture, disease indicator, or both texture and disease indicator as the feature representing in the first imaging data. The COPD information may be determined in response to the input of a geometric characteristic of the airways from the modeling.

Any of various types of machine learning, architectures, and/or corresponding machine-learned models may be used, such as a convolutional neural network. In other embodiments, statistical analysis is used to identify the inputs relationship to the COPD information and the relationships are used to relate patient-specific inputs to the COPD information. For example, a variable for the input more determinative of the COPD information than other variables for the input is identified and used for diagnosis and/or therapy.

In one embodiment, the more comprehensive collection of information for airway modeling and determination of COPD information is selected to be performed based on analysis of the patient questionnaire answer and the spirometry result.

In a second aspect, a system is provided for chronic obstructive pulmonary disorder (COPD) assessment. A medical scanner is configured to scan lungs of a patient, resulting in image data representing the lungs of the patient. An image processor is configured to generate, with a machine-learned model, a COPD indication in the lungs from a flow model based on segmentation of airways represented in the image data and based on a feature of the lungs represented in the image data. The feature may be a texture or imaging-based indication of a disease. A display is configured to display the COPD indication.

In one embodiment, the medical scanner is a CT scanner including the image processor. The machine-learned model may be a convolutional neural network or other machine-learned model.

In another embodiment, other inputs are used to generate the COPD indication. For example, the image processor is configured to generate the COPD indication from the flow model, the feature, a spirometry result for the patient, and a questionnaire answer for the patient. Any COPD indication may be generated, such as a COPD severity, a COPD diagnosis, a COPD therapy, a COPD quantification, a COPD exacerbation risk, or combinations thereof.

In a third aspect, a method is provided for chronic obstructive pulmonary disorder (COPD) assessment in a medical imaging system. An airway is segmented from CT data. Airflow in the airway is determined with computational fluid dynamics, and an image feature is determined from the CT data. COPD data is generated from the airflow and the image feature and displayed.

In one embodiment, the COPD data is generated from application of the airflow, the image feature, a questionnaire answer, and a spirometry result to a machine-learned model.

The present invention is defined by the following claims, and nothing in this section should be taken as a limitation on those claims. Further aspects and advantages of the invention are discussed below in conjunction with the preferred embodiments and may be later claimed independently or in combination. Aspects of one type (e.g., a method) may be applied to other types (e.g., other methods, systems, or computer readable media).

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Artificial intelligence (AD-based assessment of COPD uses airflow modeling. More accurate diagnosis and/or quantification of COPD progression and/or severity for patient diagnosis and/or treatment is provided by unification with high-dimension data features, such as large airway features (anatomic and airflow) from airway modeling, mid-to-distal airway features (anatomic and airflow) from airway modeling, features attained through medical imaging, spirometry features, and/or data acquired from a questionnaire. This AI tool integrates medical imaging (CT), airflow simulations (Computational Fluid Dynamics to capture the hemodynamics), spirometry measurements, and machine learning to better understand crucial characteristics of COPD. This increased understanding and predictability may provide patients with higher quality of life (better preliminary identification of disease risk, diagnosis, management, etc.), reduce costs of treatment related COPD expenditure, and open a gateway for new studies to be carried out towards understanding the pathology more thoroughly.

By isolating features of the disease previously inseparable, correlations with each respective feature may be made. For example, in some patients with chronic asthma, a clear distinction from COPD is not possible using current imaging and physiological testing techniques. This AI tool may achieve the ability to distinguish asthma from COPD through training from a large set of data with a combination of inputs (e.g. flow, spirometry, medical images, and questionnaire answers) in machine learning analysis.

Figure 1:
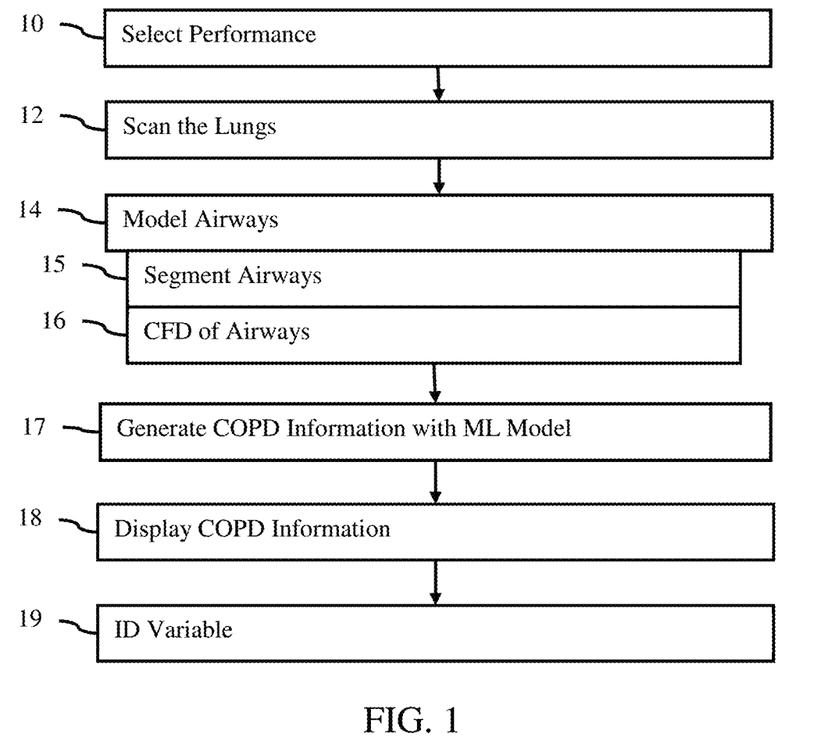
FIG. 1 is a flow chart diagram of one embodiment of a method for chronic obstructive pulmonary disorder (COPD) assessment in a medical imaging system.

FIG. 1 shows a method for COPD assessment in a medical imaging system. Various input variables, including values for hemodynamic characteristics of the airflow in the airways, are used to assess COPD. The airway modeling in combination with CT or other medical imaging provides data to determine COPD information.

Figure 2:
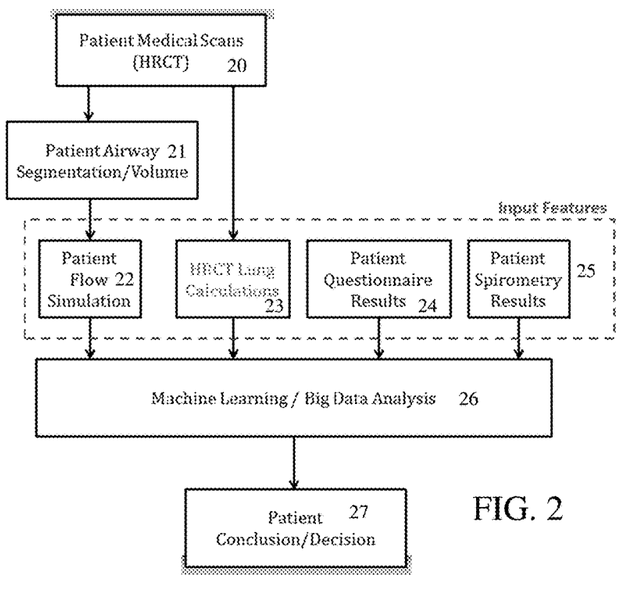
FIG. 2 is an example representation of data flow in the method of FIG. 1.

FIG. 2 shows a block diagram showing the workflow or data flow for FIG. 1. This data flow integrates a combination of input features for the purpose of compiling a rich set of data for a comprehensive look into the nature of COPD. Different, additional, or fewer types of input features may be used.

The method of FIG. 1 is implemented in the order shown (e.g., top to bottom or numerical) or a different order. Additional, different, or fewer acts may be performed. For example, acts 10, 18, and/or 19 may be omitted. As another example, act 14 may be performed without performing acts 15 and/or 16. Acts for configuring the scanner, other medical imaging, and/or diagnosis workflow may be provided.

The method is implemented by a medical imaging system, such as any system for image processing from medical scans. The medical imaging system may be medical diagnostic imaging system, a review station, a workstation, a computer, a picture archiving and communication system (PACS) station, a server, a mobile device, combinations thereof, or another image processor. For example, the system shown in or described for FIG. 4 implements the method, but other systems may be used. A hardware image processor of any type of system, interacting with memory (e.g., PACS database or cloud storage), display, and/or medical scanner, may perform the acts.

In act 10, an initial assessment is performed. The image processor, with or without input from a user, selects whether to perform acts 12, 14, 17, and/or 18. For example, an initial assessment is performed for a particular patient. If the assessment shows possible COPD, then further assessment is to be performed based on imaging and/or airway modeling. If the assessment shows COPD or no COPD with sufficient confidence, then the cost of further assessment may be avoided. Where the assessment indicates possible COPD, then the scanning of act 12, modeling of act 14, and determination of act 17 are performed.

Any information may be used for the initial assessment. For example, one or more answers to one or more questions in a COPD questionnaire are used. As another example, one or more results from spirometry are used. In other examples, both answers and results are used in combination.

Any assessment may be used. For example, a plurality of thresholds to different results and/or answers are applied. As another example, fuzzy logic or other logic progression using the results and/or answers are applied. In yet another example, a machine-learned model is trained to perform the initial assessment from the results and/or answers. For example, a machine-learned classifier determines if a patient requires medical imaging or not for COPD assessment based on their respective spirometry and active symptoms.

In act 12, a medical scanner scans the lungs of a patient. Herein, plural lungs are used, but a single lung or partial lung may be scanned. The medical scanner generates high resolution (e.g., 4 mm or higher) imaging data 20 representing an interior of a patient. The image or imaging data is made available by or within the medical scanner. Alternatively, the acquisition is from storage or memory, such as acquiring a previously created dataset from a PACS. A processor may extract the data from a PACS or a medical records database.

The data may be in any format. While the terms image and imaging are used, the image or imaging data may be in a format prior to actual display of the image. For example, the medical imaging data may be a plurality of scalar values representing different locations in a Cartesian or polar coordinate format different than a display format. As another example, the medical image may be a plurality red, green, blue (e.g., RGB) values output to a display for generating the image in the display format. The medical image may be currently or previously displayed image in the display or another format. The imaging data is a dataset that may be used for imaging, such as scan data or a generated image representing the patient.

Any type of medical imaging data and corresponding medical scanner may be used. In one embodiment, the high resolution imaging data 20 is a computed tomography (CT) image acquired with a CT system. For example, a chest CT dataset may be acquired by scanning the lungs using an x-ray source and detector mounted to a moveable gantry. For CT, the raw data from the detector is reconstructed into a three-dimensional representation by an image processor. As another example, magnetic resonance (MR) data representing a patient is acquired with an MR system. The data is acquired using an imaging sequence for scanning a patient. K-space data representing an interior region of a patient is acquired. Fourier analysis is performed to reconstruct the data from the k-space into a three-dimensional object or image space. The data may be ultrasound data. Beamformers and a transducer array scan a patient acoustically. The polar coordinate data is detected and beamformed into ultrasound data representing the patient.

The medical imaging data represents tissue and/or bone structure of the patient. For imaging the lungs, the imaging data may include response from the lungs and the anatomy around the lungs (e.g., upper torso). The data representing the lungs may be segmented so that data representing other parts of the patient is not included. The medical imaging or scan data may be normalized for scale and/or dynamic range.

The medical imaging data represents a multi-dimensional region of the lungs, such as a two or three-dimensional region of the patient. For example, the medical imaging data represents an area or slice of the patient as pixel values. As another example, the medical imaging data represents a volume or three-dimensional distribution of voxels. The three-dimensional representation may be formatted as a stack or plurality of two-dimensional planes or slices. Values are provided for each of multiple locations distributed in two or three dimensions. The medical imaging data is acquired as one or more frames of data. The frame of data represents the scan region at a given time or period. The dataset may represent the area or volume over time, such as providing a four-dimensional (4D) representation of the patient.

In one embodiment, imaging data is acquired for both inspiratory and expiratory scans. Inspiratory scans show emphysema by evaluating low-attenuation areas. Expiratory scans may be used to detect both emphysema and small airway disease, which is not as clearly visible in the inspiratory scans via gas-trapping regions (<−850 HU). In other embodiments, only expiratory scans, only inspiratory scans, or scans at other times in the breathing cycle are used.

In act 14, the image processor models airways of the lung of the patient. The modeling represents the airways of the patient. Any type of modeling may be used. For example, a mesh is formed to represent the airways in 3D. As another example, a 3D model is fit to the airways of the patient. The 3D model may be a biomechanical model. Physics models or models with other parameterization may be used. In other embodiments, a simplified model is used. For example, centerlines of the airways are found. As another example, a reduced order model, such as representing resistance and/or other characteristics of the airways is formed. The models may include boundary conditions based on an average or default values for geometry and/or airflow. Alternatively, the boundary conditions are based on modeling, such as representing larger and/or medium airways with a 3D model and representing smaller airways with a reduced order model as the boundary conditions for the larger and/or medium airways. Spirometry results may be used to determine the boundary conditions. Any threshold or thresholds for separating larger and smaller or larger, medium, and smaller may be used, such as thresholds based on airway average diameter. Other modeling may be used.

The modeling is from the imaging data. The model is fit to and/or extracted from the imaging data. The imaging data represents the airways of the patient. By using the imaging data, the modeling is specific to the patient. Image processing is used to personalize the model to the imaging data.

The modeling provides a value for airflow in the airways. The personalized model is used to provide a value for the airflow in the airways and/or for anatomy of the airways. For anatomy, the geometry provided by the model or indicated by a value or values of the personalized model may be extracted. For example, a % obstructed for each airway is calculated from the smallest diameter of the airway relative to an average diameter of the airway. Other obstruction calculations may be used. As another example, a maximum, minimum, median, or other statistic of the diameter of each airway or groups of airways is determined. Other geometrical or anatomical characteristics of the airways may be determined.

For airflow, the personalized model may indicate the rate (e.g., velocity), acceleration, volume flow, change in flow, change in volume, pressure, loss of pressure, shear, shear stress, and/or other flow characteristic. The personalized model is used to simulate the flow 22 of air. The airflow may be calculated from stored values selected based on the fit of the model to the imaging data for the patient. Alternatively, the airflow is calculated using computational fluid dynamics.

In FIG. 1, an example of modeling of act 14 is shown in acts 15 and 16. In act 15, the airways are segmented 21 from the imaging data for the patient. A threshold may be applied to segment 21 airway locations from other locations. The resulting airway indications may be spatially filtered, such as low pass filtered or directionally filtered. Random walker from one or more airway seed locations or other segmentation 21 may be used. In another example, a machine-learned classifier classifies each voxel as representing an airway or not. Adjacent voxels labeled as airway are then connected to form the airway. Any segmentation 21 for lung airways may be used, such as segmentation 21 approaches for segmenting the airways for a patient from CT data.

Figure 3:
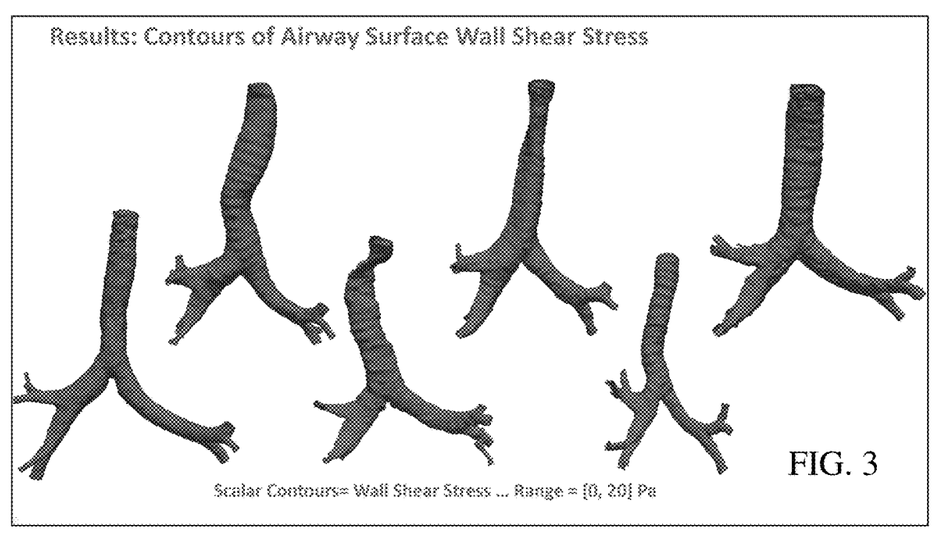
FIG. 3 is an example output of airway modeling.

In act 16, the image processor performs computational flow dynamics (CFD) as a simulation 22 of airflow for the airways. The airflow in the airways is determined with CFD. Using boundary conditions and the modeling (e.g., 3D airway tree and/or reduced order model), values for characteristics of the airflow through the airways of the airway tree are determined. FIG. 3 shows example surface wall shear stress from CFD modeling of different airways for a patient. The grayscale indicates the magnitude of the stress by location on the 3D surface of the airways.

Other inputs or features relating to COPD are determined. The image processor determines 23 a value or values for one or more image features. For example, a value or values by voxel or groups of voxels represent the texture provided in the CT data. A statistical feature, such as variance, may be used for the texture feature. Pattern matching may be used to identify specific textures from a library of patterns. In other examples, one or more indicators of disease, whether COPD or other disease, are detected. The severity, size, or binary detection are used as the value or values for the image features. In one embodiment, a machine-learned detector is applied to detect scare tissue, tumors, and/or other indicator of disease and/or severity of disease. Alternatively, the image data from the scans 20 is input to the machine-learned model for COPD assessment, where the machine-learned model extracts deep learned features as the image features.

Other input features may be answers 24 from questionnaires. For example, answers regarding family history, previous diagnosis, being a smoker or not, level of exercise, or another answer 24 to a question on a COPD questionnaire is used as the value or values. Other input features may be measures of pulmonary function, such as inhalation and/or exhalation volume and/or rate. The values of pulmonary function may be for spirometry results 25, such as measures for response to drug application.

In act 17, the image processor generates 26 COPD data 27. COPD is information generated by the processor in response to the values of the input features. The COPD information indicates a characteristic of COPD relative to the patient. The characteristic may be existence of COPD (e.g., COPD diagnosis), a severity, a COPD quantification (e.g., COPD gold level, amount of reduction in lung function, and/or total lung function), a COPD therapy to be used (e.g., change in lifestyle, medication, none, use of oxygen, and/or other treatment), or combinations thereof. Other example COPD information includes a prognosis, such as chance of survival and/or risk of exacerbation over a time period. For risk of exacerbation, the amount and/or timing of sudden increase in symptom severity may be predicted.

The image processor generates the COPD data from application of the airflow, the image feature, a questionnaire answer, a spirometry result, and/or another type of feature. One or more values for one or more of each or some types of features may be used. The application provides the COPD information, such as through a look-up table or function relating the input values to the COPD information output. By using multiple sources of input features, the COPD information may be more meaningful than spirometry interpretations as spirometry metrics are only loosely correlated to disease stage. Better diagnosis on mild COPD patients (current COPD GOLD diagnosis is known to mark unhealthy patients as healthy) may be provided.

In one embodiment, the input values are applied to a machine-learned model. In response to input of the values for the airflow from modeling, a patient questionnaire answer, a spirometry result, and/or a value of a feature represented in the imaging data or the imaging data, the machine-learned model outputs the COPD information. In one example, the value or values from airway modeling (e.g., airway geometry/anatomy and/or airflow) in combination with at least image data (e.g., one or move values for one or more image features (e.g., texture and/or disease indicator)) are applied to the machine-learned model, which outputs the COPD information in response.

The image processor applies the machine-learned model to the input data or feature vector. The values of the inputs are input to the machine-learned model. The application results in creation of values for COPD information, such as a GOLD score or binary (yes/no) diagnosis.

Any machine-learned model may be used. In one embodiment, the machine-learned model is a convolutional neural network. For example, the convolutional neural network is a deep learned model using restricted Boltzmann machines, deep belief network, neural autoregressive density estimators, variational auto-encoders, extensions thereof, or other deep learning approaches. Any layer architecture may be used with any types of layers, such as fully connected layers, max pooling, other pooling, global averaging, linear-sigmoid, SoftMax, and/or convolutional. Feedforward (e.g., in a dense net), skip, and/or feedback connections between layers may be used.

The model is trained to generate the COPD information. Many samples of collections of input values for input features and corresponding ground truth COPD information are used to machine train the model. The defined machine-learning architecture is trained with the ground truth. Each sample of CT scan or imaging data and airway model output with or without other inputs is labeled with ground truth COPD information. The ground truth is from expert or physician determination, measures using a breath tube (inhalation or exhalation measures) in a pulmonary function test, or other source. The GOLD scores may be used. The GOLD score for each sample is thresholded to find a binary classification of COPD or not (e.g., 0=no COPD and 1-4=COPD). Alternatively, the COPD score is used as the ground truth to classify into one of five classes (0-5 GOLD score).

For training the model, a computer, workstation, server, or other processor accesses a database of hundreds or thousands of example inputs with known COPD information (e.g., yes/no or GOLD score). The machine learns the values of variables of the architecture (e.g., the convolutional neural network) from the example inputs and ground truth of the database. Using a piecewise-differentiable function or other deep learning function, the machine trains the model to learn to relate input values to output COPD information.

To train, the log-likelihood of the output is maximized. The model encodes features (i.e., kernels of the convolution layers), weights, connections, and/or other parameters. The neural network is trained with deep machine learning to output the COPD information. Any loss function, such as L1 or L2, may be used. The loss function may be for binary classification for loss, such as a L1 loss based on correct estimation as the patient having COPD or not. The loss function may be for any number of classes or for other COPD information, such as the type of COPD or therapy to be applied for COPD. Any optimization, such as Adam or Ada, may be used in training using the training data and loss function.

In alternative embodiments, other types of architectures and/or machine learning are used. For example, a support vector machine or Bayesian network are used.

The machine-learned model is stored in the memory with the training data or other memory. For example, copies of the machine-learned model are distributed to or on different medical scanners for use in hospitals or medical practices. As another example, copies are stored in a memory of one or more servers for COPD diagnosis assistance as a service or for remote COPD diagnosis assistance.

Once trained, the machine-learned model is applied. The input values for a particular patient are input. The machine-learned model outputs the COPD information for that patient in response to the input. For example, COPD information is output in response to the input of texture or image data, disease indicator, geometric characteristic of airways, airflow values, spirometry results, and/or questionnaire answers.

In act 18, the image processor generates an image with the COPD information. The image is output to a display device to display the COPD information for the patient. The COPD data, such as diagnosis, quantity, therapy, prognosis, or exacerbation risk, is displayed. The image may include an alphanumeric or graphical representation of the COPD information, such as the non-spatial or global estimate output by the machine-learned model.

The scan data may be used to generate an image of the lungs. The image may be a cross-section through the lungs. Alternatively, the image is a rendering of the three-dimensional distribution to a two-dimensional display, 3D holographic display, an augmented reality display, or virtual reality display. The COPD information may be an annotation overlaid on or adjacent to the image of the lungs. Alternatively, the image is of a medical report that includes the COPD information.

The COPD information may be used for patient scheduling based on a patient-specific need. The viewer of the COPD information schedules. Alternatively, the image processor or other processor indicates a scheduling recommendation and/or schedules. The processor searches for available times for treatment, follow-up, or another appointment and schedules based on immediacy indicated by the COPD information. For example, based on the learned correlations from the big-data machine learning analysis, new biomarkers may be identified to guide clinician's decision to schedule more, or less, frequent assessments and appointments with patients based on their current and foreseeable condition output as COPD information.

In act 19, the processor identifies one or more variables for the input features that are more determinative of the COPD information than other variables for the input. One or more input features to the machine-learned model are identified. By randomly or in a pattern varying values of different variables, the magnitude of the effect of variation on the output COPD information is determined. Alternatively, the machine learning identifies correlations between inputs and the output, which correlations are extracted from the machine learning to identify the variable or variables of particular importance. For example, based on the learned correlations from the big-data machine learning analysis, new biomarkers or other input features may be established to guide clinicians' decisions, such as guiding the clinician to schedule more, or less, frequent assessments and appointments with patients based on their current and foreseeable condition.

Figure 4:
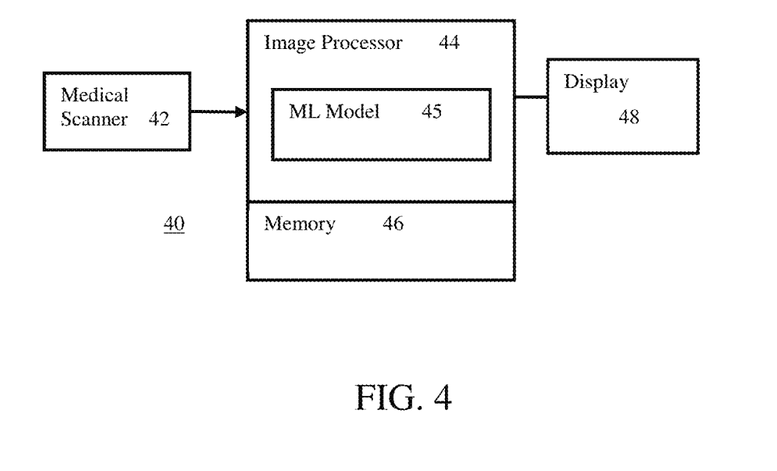
FIG. 4 is a block diagram of one embodiment of a system for COPD assessment.

FIG. 4 shows a system 40 for COPD assessment. The system 40 implements the method of FIG. 1, the workflow or dataflow of FIG. 2, or another method. The system 40 is for application of a machine-learned model 45. Given input imaging data, the system 40 models the airways of the patient and uses the machine to generate one or more COPD indications from values of the imaging data and airway modeling. The COPD indication is COPD information or other information indicating a characteristic of COPD for the patient. While the system 40 is described below in the context of application of the previously learned model, the system 40 may be used to machine train the model.

The system 40 includes an image processor 44, a memory 46, a display 48, and a medical scanner 42. The image processor 44, memory 46, and display 48 are shown separate from the medical scanner 42, such as being part of a workstation, computer, or server. In alternative embodiments, the image processor 44, memory 46, and/or display 48 are part of the medical scanner 42. In yet other embodiments, the system 40 does not include the medical scanner 42. Additional, different, or fewer components may be used.

The medical scanner 42 is a CT, MR, ultrasound, or another type of scanner for scanning a lung of a patient. In one embodiment, the medical scanner 42 is a CT system with an x-ray source and detector mounted to a moveable gantry for three-dimensional scanning of the upper torso of the patient. The image processor 44 or other processor of the medical scanner 42 performs computed tomography to determine scalar values for the tissue response to the x-rays in three dimensions.

The scan provides the scan data representing the lungs. The medical scanner 42 is configured by user settings or presets to scan the lungs of the patient, resulting in scan data representing all or at least part of the lungs of the patient. This imaging data is in any format, such as scalar values distributed in a regular or evenly dispersed 3D grid (i.e., uniform voxels).

The memory 46 is a buffer, cache, RAM, removable media, hard drive, magnetic, optical, database, or other now known or later developed memory. The memory 46 is a single device or group of two or more devices. The memory 46 is shown associated with or part of the image processor 44 but may be outside or remote from other components of the system 40. For example, the memory 46 is a PACS database storing the scan data from the medical scanner 42.

The memory 46 stores the image data, a machine-learned model 45, values of features, airway model, segmentation, COPD information, and/or information used in image processing to generate the COPD information. The inputs and/or outputs to the airway model and/or the machine-learned model are stored. For training, the training data (e.g., scan data, airway model values, spirometry results, questionnaire answers, and ground truth COPD data) are stored in the memory 46.

The memory 46 is additionally or alternatively a non-transitory computer readable storage medium with processing instructions. The memory 46 stores data representing instructions executable by the programmed image processor 44. The instructions for implementing the processes, methods and/or techniques discussed herein are provided on computer-readable storage media or memories, such as a cache, buffer, RAM, removable media, hard drive or other computer readable storage media. The machine-learned generative network may be stored as part of instructions for classification or map generation. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 44 is a general processor, digital signal processor, three-dimensional data processor, graphics processing unit, application specific integrated circuit, field programmable gate array, digital circuit, analog circuit, artificial intelligence processor, combinations thereof, or other now known or later developed device for generating a COPD indication by application of a machine-learned model or network 55. The image processor 44 is a single device, a plurality of devices, or a network. For more than one device, parallel or sequential division of processing may be used. Different devices making up the image processor 44 may perform different functions, such as one processor performing segmentation and CFD for airway modeling and another processor applying the machine-learned model 45. In one embodiment, the image processor 44 is a control processor or other processor of a medical diagnostic imaging system (e.g., medical scanner 42). The image processor 44 is a hardware device configured by or operating pursuant to stored instructions, design (e.g., application specific integrated circuit), firmware, or hardware to perform various acts described herein.

The image processor 44 is configured to generate, with the machine-learned model 45, the COPD indication in the lungs from a flow model based on segmentation of airways represented in the image data and based on a feature of the lungs represented in the image data. The image processor 44 segments the airways and personalizes an airway model to the segmented airways. CFD is used to determine the value or values for various features from the personalized airway model. The anatomy and/or airflow for the airways of the patient are determined. The image or scan data may be image processed to determine values of one or more features. Alternatively, the image or scan data is input as the image feature to the machine-learned model 45, which uses convolution and/or other activations to determine values for features of the image data. Spirometry results and/or questionnaire answers may be input, loaded from a medical record, or mined from laboratory database by the image processor 44. Other input data may be acquired.

To generate the COPD indication, the values for the various input features are applied to the machine-learned model. The machine-learned model, such as a machine-trained convolutional neural network, generates the COPD indication. The flow model, input or machine-learned model extracted image feature, spirometry results for the patient, questionnaire answers for the patient, and/or other input values are used by the machine-learned model to output the COPD indication. The output COPD indication may be a COPD severity, a COPD diagnosis, a COPD therapy, a COPD quantification, a COPD exacerbation risk, or combinations thereof.

The image processor 44 may generate an image. The generated COPD indication (e.g., classification) is used to generate an image. The image may include an image of the lungs generated from the image data. The image is of the lungs of the patient with highlighting, a graph, or annotation providing the COPD indication.

The display 48 is a CRT, LCD, plasma, projector, printer, or other output device for showing the COPD indication, such as an image or other output of the image processor 44 and/or medical scanner 42. The display 48 displays an image that includes the COPD indication or indications. The image may include an annotation for the image or scan region level, global or patient generalized estimate, or location-specific estimate of COPD indication.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for chronic obstructive pulmonary disorder (COPD) assessment in a medical imaging system, the method comprising:
    scanning, by a medical scanner, a lung of a patient, the scanning providing first imaging data representing a multi-dimensional region of the lungs of the patient;
    modeling, by an image processor, airways of the lung of the patient from the first imaging data, the modeling providing a value for airflow in the airways;
    determining, by the image processor, COPD information from a machine-learned model in response to input of the value for the airflow, a patient questionnaire answer, a spirometry result, and a value of a feature represented in the first imaging data; and
    displaying the COPD information for the patient.

2. The method of claim 1 wherein scanning comprises scanning with the medical scanner being a computed tomography system, and wherein the multi-dimensional region comprises a three-dimensional region.

3. The method of claim 1 wherein modeling comprises segmenting the airways of the lung from the first imaging data.

4. The method of claim 1 wherein modeling comprises performing computational flow dynamics for the airways, the value for the airflow comprising a stress, pressure, velocity, or volume value.

5. The method of claim 1 wherein modeling comprises modeling a first portion of the airways with a three-dimensional model and a second portion of the airways with a reduced order model, the second portion having the airways with smaller diameters than the airways of the first portion.

6. The method of claim 1 wherein determining comprises determining a COPD severity as the COPD information.

7. The method of claim 1 wherein determining comprises determining a COPD quantification as the COPD information.

8. The method of claim 1 wherein determining comprises determining a COPD diagnosis, COPD therapy, or both COPD diagnosis and COPD therapy as the COPD information.

9. The method of claim 1 wherein determining comprises determining in response to the input of texture, disease indicator, or both texture and disease indicator as the feature representing in the first imaging data.

10. The method of claim 1 wherein determining comprises determining in response to the input of a geometric characteristic of the airways from the modeling.

11. The method of claim 1 further comprising selecting performance of the scanning, the modeling, and the determining based on the patient questionnaire answer and the spirometry result.

12. The method of claim 1 wherein determining comprises determining with a convolutional neural network as the machine-learned model.

13. The method of claim 1 further comprising identifying a variable for the input more determinative of the COPD information than other variables for the input.

14. A system for chronic obstructive pulmonary disorder (COPD) assessment, the system comprising:
    a medical scanner configured to scan lungs of a patient, the scan resulting in image data representing the lungs of the patient;
    an image processor configured to generate, with a machine-learned model, a COPD indication in the lungs from a flow model based on segmentation of airways represented in the image data and based on a feature of the lungs represented in the image data; and a display configured to display the COPD indication.

15. The system of claim 14 wherein the medical scanner comprises a computed tomography scanner including the image processor.

16. The system of claim 14 wherein the machine-learned model comprises a convolutional neural network.

17. The system of claim 14 wherein the image processor is configured to generate the COPD indication from the flow model, the feature, a spirometry result for the patient, and a questionnaire answer for the patient.

18. The system of claim 14 wherein the COPD indication comprises a COPD severity, a COPD diagnosis, a COPD therapy, a COPD quantification, a COPD exacerbation risk, or combinations thereof.

19. A method for chronic obstructive pulmonary disorder (COPD) assessment in a medical imaging system, the method comprising:

segmenting an airway from computed tomography (CT) data;

determining airflow in the airway with computational fluid dynamics and determining an image feature from the CT data;

generating COPD data, with a machine-learned model, from the airflow and the image feature; and displaying the COPD data.

20. The method of claim 19 wherein generating comprises generating from application of the airflow, the image feature, a questionnaire answer, and a spirometry result to the machine-learned model.

* * * * *